United States Patent [19]
Thorsell et al.

[11] 4,192,892
[45] Mar. 11, 1980

[54] AROMATIC α-HYDROXYAMIDES WITH INSECT REPELLENT PROPERTIES

[76] Inventors: Walborg Thorsell, 45 Karlskronavagen, Johanneshov, Sweden, S-121 52; Maarja Mikiver, 46 Hagalundsgatan, Solna, Sweden, S-171 50; Elisabeth Malm, 8 Gaddvagen, Järfälla, Sweden, S-175 47; Lennart Wennberg, 51 Rankhusvägen, Kungsängen, Sweden, S-196 31

[21] Appl. No.: 925,975

[22] Filed: Jul. 19, 1978

Related U.S. Application Data

[63] Continuation of Ser. No. 784,563, Apr. 4, 1977, abandoned.

[30] Foreign Application Priority Data

Apr. 6, 1976 [SE] Sweden ................................ 7604030

[51] Int. Cl.² .............................................. A01N 9/20
[52] U.S. Cl. .................................. 424/324; 260/559 R; 424/DIG. 10
[58] Field of Search .................... 260/559 R; 424/324, 424/DIG. 10; 544/238, 242, 406, 391; 546/192

[56] References Cited

U.S. PATENT DOCUMENTS 3,344,188  9/1967  Wollweber et al. ................. 260/559
3,966,809  6/1976  Baker et al. ......................... 424/324

Primary Examiner—Winston A. Douglas
Assistant Examiner—J. V. Howard
Attorney, Agent, or Firm—Meyer, Tilberry & Body

[57] ABSTRACT

Aromatic α-hydroxyamides are disclosed, which are useful as active components in insect repellent compositions. Suitable compounds are derivatives of mandelic acid amide, such as N,N-diethyl-D,L-mandelic acid amide.

8 Claims, No Drawings

AROMATIC α-HYDROXYAMIDES WITH INSECT REPELLENT PROPERTIES

This is a continuation of application Ser. No. 784,563, filed Apr. 4, 1977, now abandoned.

The present invention is directed to aromatic α-hydroxyamides, which are useful as active components in insect repellent compositions, and to a method to protect articles, animals and persons against insects.

Insect repellents cause dangerous insects to avoid attractive articles, animals or persons treated with repellent. The protection thus obtained, does not appreciably disturb the sensitive balance in nature. Such a protection prevents insect stings and bites thus inhibiting the transfer of different insect borne diseases, such as malaria, yellow fever, filariasis, tularemia, encephalitis, typhus; diseases, which every year cause the death of millions of persons. Secondarily the appearance of infections, allergic reactions and/or irritation is prevented. On the other hand insecticidal compounds do not prevent insects to approach attractive articles or persons. Such substances also need a certain latency time for their effect and do not directly protect against insect stings or bites and the troubles thus caused.

Among the mostly used insect repellents N,N-diethyl-m-toluamide (DEET) and the less effective 2-ethyl-1,3-hexanediol may be mentioned. Also for man more dangerous compounds, such as dimethylphthalate, are used as repellents. DEET fulfills the requirements upon a good insect repellent only to some extent. It penetrates the skin, it irritates mucous membranes and is accumulated in the organism and has a smell unpleasant to some people. It is used in high concentrations for obtaining a long time effect. In high concentrations it also affects synthetic materials unfavourably.

The present invention is directed to compounds which are insect repellent and besides have more physiologically acceptable properties than previously used repellents. The present compounds have hydrophilic as well as lipophilic character, which is considered to be of advantage with regard to the absorption and metabolism of the repellents within the organism. The compounds are tolerated on skin and mucous membranes, are colourless and almost without smell. They have a low vapour pressure, which contributes to a slow evaporation from treated surfaces. Besides the compounds have a pronounced long term effect, also at low concentrations. The good insect repellent effect at low concentrations helps to negate of unfavourable effects on synthetic material. Since the compounds are of amide nature they are comparatively stable and are not rapidly hydrolyzed e.g. by perspiration.

The compounds of the present invention have the general formula (I)

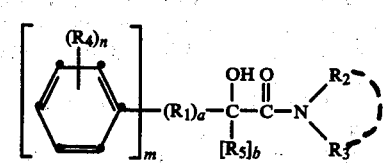

wherein $R_1$ is carbonyl, straight or branched $C_1$-$C_{10}$-alkylene, $C_2$-$C_{12}$-alkenylene, $C_1$-$C_{10}$-alkanyl-ylidene, $C_2$-$C_{12}$-oxoalkylene, $C_3$-$C_{13}$-oxoalkenylene or $C_2$-$C_{12}$-oxoalkanyl-ylidene, and optionally substituted with $C_1$-$C_{10}$-alkyl, methylene, $C_2$-$C_{10}$-alkenyl, $C_1$-$C_{10}$-alkoxy, hydroxy, $C_1$-$C_{10}$-hydroxyalkyl, $C_2$-$C_{10}$-hydroxyalkenyl, $C_1$-$C_{10}$-hydroxyalkoxy; $R_2$ and $R_3$ independently are $C_1$-$C_{10}$-alkyl or $C_2$-$C_{10}$-alkenyl, or $R_2$ and $R_3$ form together a ring with 5–10, preferably 5–6, ring atoms, which ring may contain further hetero atoms, such as N, S or O, and optionally is lower alkyl and/or lower alkenyl substituted; $R_4$ is hydroxy, $C_1$-$C_{10}$-alkyl or $C_1$-$C_{10}$-alkoxy; $R_5$ is hydrogen, $C_1$-$C_{10}$-alkyl, $C_1$-$C_{10}$-alkoxy or phenyl; a is an integer equal to 0 or 1; b is an integer equal to 0, when $R_1$ is alkanyl-ylidene, and equal to 1, when $R_1$ is as otherwise defined above; m is an integer equal to 1–3 and n is an integer equal to 0–3.

(1) Suitable compounds are compounds of the formula (I) wherein $R_1$ is carbonyl, straight or branched $C_1$-$C_{10}$-alkylene or $C_2$-$C_{12}$-oxoalkylene and optionally substituted with $C_1$-$C_{10}$-alkyl, $C_1$-$C_{10}$-alkoxy, hydroxy, $C_1$-$C_{10}$-hydroxyalkyl or $C_1$-$C_{10}$-hydroxyalkoxy; $R_2$ and $R_3$ are as defined above except for $C_2$-$C_{10}$-alkenyl and provided that a ring formed by $R_2$ and $R_3$ cannot be lower alkenyl substituted.

(2) Suitable are also compounds of formula (I), wherein $R_1$ is carbonyl, straight or branched $C_1$-$C_6$-alkylene, $C_2$-$C_8$-alkenylene, $C_1$-$C_6$-alkanyl-ylidene, $C_2$-$C_8$-oxoalkylene, $C_3$-$C_9$-oxoalkenylene or $C_2$-$C_8$-oxoalkanyl-ylidene and optionally is substituted with lower alkyl, methylene, lower alkenyl, lower alkoxy, hydroxy, hydroxy lower alkyl, hydroxy lower alkenyl or hydroxy lower alkoxy; $R_2$ and $R_3$ independently are hydrogen, lower alkyl or lower alkenyl; $R_4$ is hydroxy, lower alkyl or lower alkoxy and $R_5$ is hydrogen, lower alkyl or lower alkoxy.

(2A) Among compounds included in group (2) those are preferred wherein $R_1$ is straight or branched $C_1$-$C_6$-alkylene or $C_2$-$C_8$-oxoalkylene and optionally is substuted with lower alkyl, lower alkoxy, hydroxy, hydroxy lower alkyl or hydroxy lower alkoxy, and $R_2$ and $R_3$ independently are hydrogen or lower alkyl, and preferably m is equal to 1.

(2B) Particularly suitable are compounds included in group (2A) wherein $R_1$ is straight or branched $C_1$-$C_6$-alkylene, optionally substituted with lower alkyl, lower alkoxy, hydroxy, hydroxy lower alkyl or hydroxy lower alkoxy; $R_5$ is hydrogen, m is equal to 1 and n is equal to 0.

(2C) Among compounds included in groups (2B) are those wherein $R_2$ and $R_3$ are identical and are lower alkyl particularly suitable.

(2D) Among compounds included in group (2B) are those preferred wherein a is equal to 0. Preferably $R_2$ and $R_3$ are then identical and are lower alkyl.

As is evident from the formula (I) the α-carbon atom is assymetric when b is equal to 1. Thus the compounds are present as D-, L- or DL-forms, When b is equal to 0 the compounds of the formula (I) exist in two tautomeric forms, viz. enol- and keto-form. The present invention is directed to all these isomeric forms.

In the definition of $R_1$ "alkylene" means a bivlent group derived by the removal of one hydrogen atom from two different carbon atoms of an alkane. One exception is of course methylene, which is obtained by removal of two hydrogen atoms from the same carbon atom. Examples of short chained alkylenes which may be mentioned are methylene (—$CH_2$—), ethylene (—$CH_2$—$CH_2$—), 1,2-propylene

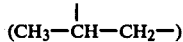

and 1,3-propylene (—CH$_2$—CH$_2$—CH$_2$—). Examples of long chained alkylene is butylene, pentylene and hexylene, which can be straight or branched, "Alkenylene" is defined in the same way as "alkylene" except that the hydrogen atoms are removed from an alkene. Examples of alkenylene is vinylene (—CH=CH—), propenylene (—CH$_2$—CH=CH—), butenylene, pentenylene, hexenylene and 4-propyl-2-pentenylene. Further in the definition of R$_1$ "alkanyl-ylidene" means a group derived by removal of one hydrogen atom from one carbon atom and two hydrogen atoms (so that a double bond is formed) from another carbon atom in an alkane (in case of methane the same carbon atom), wherein the double bond is the bond between the α-carbon atom in the formula (I) and the adjacent carbon atom in R$_1$. Examples of such groups are methine (—CH=), 1-ethanyl-2-ylidene (—CH$_2$—CH=) and 1-propanyl-3-ylidene (—CH$_2$—CH$_2$—CH=), 1-butanyl-4-yliden, 1-pentanyl-5-ylidene and 1-hexanyl-6-ylidene. "Oxoalkylene, oxoalkenylene and oxoalkanyl-ylidene" in the definition of R$_1$ mean alkylene, alkenylene or alkanyl-ylidene wherein a carbonyl (>C=O) substitutes a —CH$_2$—group. Examples of such groups are oxoethylene, oxopropylene, oxobutylene, oxopentylene, oxohexylene; oxopropenylene, oxobutenylene, oxopentenylene, oxohexenylene, 4-oxopropyl-2-pentenylene; —CO—CH=, 1-oxopropanyl-3-ylidene, 1-oxobutanyl-4-ylidene, 1-oxopentenyl-5-ylidene and 1-oxohexanyl-6-ylidene.

According to the present invention the expressions "lower alkyl", "lower alkenyl" and "lower alkoxy" means respectively alkyl, alkenyl and alkoxy with 1–6, and preferably 1–4, carbon atoms, all of which can be straight or branched. Examples of such groups are methyl, ethyl, propyl, isopropyl, n-butyl, s- and t-butyl, pentyl, isopentyl, neopentyl, t-pentyl, hexyl; vinyl, allyl, 1-propenyl, isopropenyl, butenyl, pentenyl, hexenyl; methoxy, ethoxy, propoxy, isopropoxy, butoxy, isobutoxy, s-butoxy, t-butoxy, pentyloxy and hexyloxy. Examples of hydroxy lower alkyl, hydroxy lower alkenyl and hydroxy lower alkoxy are the above mentioned groups wherein a hydroxy substituent has been introduced. However, lower alkenyl comprises at least two carbon atoms.

As examples of alkyl, alkenyl, and alkoxy with more than 6 carbon atoms heptyl, octyl, nonyl, decyl; heptenyl, octenyl, nonenyl, decenyl; heptenoxy, octenoxy, nonenoxy and decenoxy; which groups all can be straight or branched, can be mentioned.

Further the expression "straight or branched" in the definition of R$_1$ refers to all subsequent groups, viz. (oxo)alkylene, (oxo)alkenylene and (oxo)alkanyl-ylidene.

When R$_2$ and R$_3$ form a ring, said ring preferably is comprised only of carbon atoms except for the amide nitrogen atom. Suitable rings contain 5 to 6 ring atoms. Examples of optionally substituted rings comprising only one heteroatom, viz. nitrogen, are those which are derived from pyrrole, pyridine, piperidine, coniine and azepine. Examples of optionally substituted rings containing more than one heteroatom are those derived from pyrazole, 2-isoimidazole, triazole, isoxazole, oxazole, thiazole, isothiazole, oxadiazole, oxatriazole, dioxazole, oxathiazole, pyridazine, pyridimidine, pyrazine, piperazine, triazine, oxazine, isoxazine, oxathiazine, oxatriazine, oxadiazine, morpholine and diazepine.

A further object of the present invention is a method to protect an article, animal or a person against insect attacks by application of an effective amount of a compound of formula I or a composition or preparation comprising a compound of formula I.

The biological effect of the present compounds has been studied with regard to insect repellent properties, mosquitoes having been used in the experiments. Other biological effects studied refer to skin and mucous membrane effects. For comparison the best prior art mosquito, viz. DEET, has been used.

1. N,N-diethyl-D,L-mandelic acid amide (DEM) was studied with regard to mosquito repellent properties.

(a) Experiments in the laboratory

The test person, whose one hand had been treated with 1.0 ml of 25; 12.5; 6.3; 3.1 and 1.6% by weight of DEM or DEET, resp, in ethanol, and whose other hand had been left untreated, put both hands 4, 6 and 8 hs after treatment into test cages, containing an equal number of hungry female mosquitoes, Aedes aegypti. The number of "biting" mosquitoes per minute was estimated. The tests were performed in duplicate. The results, as is evident from table 1, indicate that DEM, contrary to DEET, is completely mosquito repellent during 8 hs at a concentration of 3.1% by weight and during 6 hs at such a low concentration as 1.6% by weight.

TABLE 1

Laboratory experiments (Aedes aegypti). Number of biting mosquitoes per minute 4, 6 and 8 hs, resp., after treatment with different concentrations of DEET (reference) and DEM.

| | 4 hs | 6 hs | 8 hs |
|---|---|---|---|
| Control | 9 ± 2 | 10 ± 2 | 8 ± 1 |
| 25 percent DEET | 0 | 0 | 0 |
| 25 percent DEM | 0 | 0 | 0 |
| 12.5 percent DEET | 0 | 0 | 1 ± 1 |
| 12.5 percent DEM | 0 | 0 | 0 |
| 6.3 percent DEET | 0 | 1 ± 1 | 2 ± 1 |
| 6.3 percent DEM | 0 | 0 | 0 |
| 3.1 percent DEET | 1 ± 1 | 2 ± 1 | 3 ± 1 |
| 3.1 percent DEM | 0 | 0 | 0 |
| 1.6 percent DEET | 2 ± 1 | 3 ± 1 | 4 ± 2 |
| 1.6 percent DEM | 0 | 0 | 2 ± 1 |

(b) Field experiment

The test person treated one fore arm with the same preparations as in the laboratory tests. The other arm was left untreated. A meadow, close to Stockholm, with a great number of mosquitoes of different Culex and Aedes species, was chosen as experiment place. The frequency of mosquito bites was noted at the same time intervals as in the laboratory experiments. The results obtained corresponded to those in the laboratory. I.e. contrary to DEET DEM was completely mosquito repellent during 6 hs at such a low concentration as 1.6% by weight and during 8 hs at a concentration of 3.1% by weight (cf. table 1).

2. The effect of DEM on the skin and mucous membranes was examined. The substance did not show any apparent effects like itch, redness, smarting pain of the skin or the mucous membranes of eyes of nose of a person 8 hs after treatment. DEET on the other hand caused redness and smarting pain of the mucous membranes.

The aromatic α-hydroxy amides of formula (I) are new compounds. They can be produced from aromatic α-hydroxy acids in a traditional way according to the following:

(1) Addition of an acidchloride, e.g. acetylchloride, to an acid, e.g. mandelic acid, in order to esterify the hydroxy group, which gives an intermediate product of the formula (II);

(2) Addition of thionylchloride to produce an acid-chloride with the formula (III);

(3) Addition of amine to produce the esteramide (IV);

(4) Addition of base of hydrolyze the ester linkage, which gives compounds of formula (I); and finally (5) Purification by destillation or crystallization.

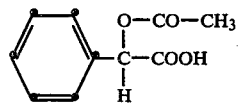 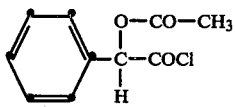 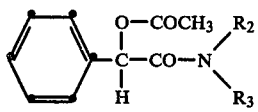

(II)  (III)  (IV)

The above described procedure has been used for the preparation of the following compounds;

| | |
|---|---|
| N,N-diethyl-D,L-mandelic acid amide | Bp.760 > 295° C. |
| N,N-dipropyl-D,L-mandelic acid amide | Mp. ≈ 52° C. |
| N,N-dibutyl-D,L-mandelic acid amide | Bp.760 > 295° C. |
| N,N-diethyl-D-mandelic acid amide | Bp.760 > 295° C. |
| N,N-dipropyl-D-mandelic acid amide | Mp. 54° C. |
| N,N-dibutyl-D-mandelic acid amide | Bp.760 > 295° C. |
| N,N-diethyl-L-mandelic acid amide | Bp.760 > 295° C. |
| N,N-dipropyl-L-mandelic acid amide | Mp. 55° C. |
| N,N-dibutyl-L-mandelic acid amide | Bp.760 > 295° C. |

The present active compounds can be used per se as well as in mixtures with other components, and they can be used for cosmetic as well as technical purposes. For cosmetic purposes they can be used e.g. as solutions, emulsions, ointments, creams, powders, pastes, sticks, spray solutions, aerosols. From a technical point of view they can be used for impregnation of e.g. different materials in clothes, tents, window frames and door posts.

Suitable preparations comprise 1.5–25% by weight of active compound(s).

Preparations containing the present compounds may further contain additives lowering the vapour pressure of the preparation, whereby a prolonged effect is obtained since the evaporation is diminished. The additive is also meant to diminish the absorption of active compound through the skin. Such additives may be high molecular compounds such as aliphatic α-hydroxyketones or alcoholesters with 16–40 carbon atoms e.g. trioctanoin, and aliphatic $C_{16}$–$C_{28}$-alcohols, especially $C_{18}$–$C_{22}$-alcohols, or aliphatic acidamides like isostearic acid amide with 16–30 carbon atoms, especially 18–22 carbon atoms. Such an effect may also be obtained by admixture of certain previously known and less active repellents such as 2-ethyl-1,3-hexanediol.

The following examples further illustrate the present invention.

EXAMPLE 1:

15 g N,N-diethyl-D,L-mandelic acid amid
85 g ethanol

The mixture can be used to impregnate different materials or be applied on the skin.

EXAMPLE 2

15 g N,N-diethyl-D,L-mandelic acid amide
30 g 2-ethyl-1,3-hexanediol
47 g ethanol
8 g trioctanoin The mixture can be used e.g. for application on the skin.

EXAMPLE 3

15 g N,N-diethyl-D,L-mandelic acid amide
30 g 2-ethyl-1,3-hexanediol
31 g glycerol
12 g sodium stearate
12 g Aerosil R 972

The mixture can be formed to a stick. It can be used for application on the skin.

What is claimed is:

1. An insect repellent composition comprising an effective amount of a compound present in the D-, L-, or DL-forms, having the general formula

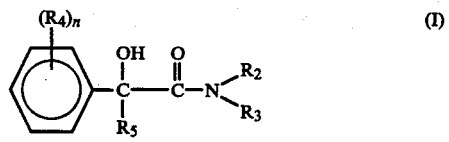

wherein, n is an integer in the range from 0 to 3;

$R_2$ and $R_3$ independently are selected from the group consisting of hydrogen, alkyl having from 1 to about 10 carbon atoms, and alkenyl having from two to about 10 carbon atoms;

$R_4$ is selected from the group consisting of hydroxy, lower alkyl having from 1 to about 5 carbon atoms, and lower alkoxy having from 1 to about 5 carbon atoms; and, $R_5$ is selected from the group consisting of hydrogen, lower alkyl having from 1 to about 5 carbon atoms, and lower alkoxy having from 1 to about 5 carbon atoms.

2. The composition of claim 1 wherein $R_2$ and $R_3$ are independently selected from hydrogen and said alkyl.

3. The composition of claim 1 wherein $R_5$ is hydrogen and n=0.

4. The composition of claim 1 wherein said compound is present in an amount in the range from about 1.5 percent to about 25 percent by weight of said composition.

5. The composition of claim 1 including an additive for lowering the vapor pressure of said composition.

6. The composition of claim 1 consisting essentially of about 15 percent N,N-diethyl-D,L-mandelic acid amide, and, 85 percent ethanol.

7. The composition of claim 1 comprising about 15 percent N,N-diethyl-D,L-mandelic acid amide, and said additive is selected from the group consisting of aliphatic alpha hydroxyketones and alcohol esters having from about 16 to about 40 carbon atoms.

8. The composition of claim 11 including 2-ethyl-1,3-hexanediol.

* * * * *